US008226691B2

(12) United States Patent
McDonnell

(10) Patent No.: US 8,226,691 B2
(45) Date of Patent: Jul. 24, 2012

(54) INSERTION GUIDE FOR A SPINAL IMPLANT

(75) Inventor: Christopher McDonnell, Sandy Hook, CT (US)

(73) Assignee: Stryker Spine (FR)

( * ) Notice: Subject to any disclaimer, the term of this patent is extended or adjusted under 35 U.S.C. 154(b) by 38 days.

(21) Appl. No.: 12/848,474

(22) Filed: Aug. 2, 2010

(65) Prior Publication Data

US 2011/0022175 A1    Jan. 27, 2011

Related U.S. Application Data

(62) Division of application No. 11/204,062, filed on Aug. 15, 2005, now abandoned.

(60) Provisional application No. 60/601,461, filed on Aug. 13, 2004.

(51) Int. Cl.
*A61B 17/88* (2006.01)

(52) U.S. Cl. ......................... 606/279; 606/99

(58) Field of Classification Search .... 623/17.11–17.16; 606/99, 90, 914–916, 86 A, 105, 279
See application file for complete search history.

(56) References Cited

U.S. PATENT DOCUMENTS

| | | |
|---|---|---|
| 3,486,505 A | 12/1969 | Morrison |
| 4,545,374 A | 10/1985 | Jacobson |
| 5,306,309 A | 4/1994 | Wagner et al. |
| 5,431,658 A | 7/1995 | Moskovich |
| 5,489,307 A | 2/1996 | Kuslich et al. |
| 5,571,109 A | 11/1996 | Bertagnoli |
| 5,676,701 A * | 10/1997 | Yuan et al. .................. 623/17.15 |
| 5,797,909 A | 8/1998 | Michelson |
| 5,895,428 A | 4/1999 | Berry |
| 5,980,522 A | 11/1999 | Koros et al. |
| 6,042,582 A | 3/2000 | Ray |
| 6,063,088 A | 5/2000 | Winslow |
| 6,080,155 A | 6/2000 | Michelson |
| 6,083,225 A | 7/2000 | Winslow et al. |
| 6,086,595 A | 7/2000 | Yonemura et al. |
| 6,113,602 A | 9/2000 | Sand |
| 6,113,638 A | 9/2000 | Williams et al. |
| 6,156,040 A | 12/2000 | Yonemura et al. |
| 6,190,387 B1 | 2/2001 | Zucherman et al. |
| 6,210,412 B1 | 4/2001 | Michelson |
| 6,224,599 B1 | 5/2001 | Baynham et al. |
| 6,224,607 B1 | 5/2001 | Michelson |
| 6,261,295 B1 | 7/2001 | Nicholson et al. |
| 6,267,763 B1 | 7/2001 | Castro |
| 6,270,498 B1 | 8/2001 | Michelson |
| 6,371,988 B1 | 4/2002 | Pafford et al. |
| 6,413,278 B1 | 7/2002 | Marchosky |

(Continued)

FOREIGN PATENT DOCUMENTS

WO    02/089701 A2    11/2002

*Primary Examiner* — Eduardo C Robert
*Assistant Examiner* — Jan Christopher Merene
(74) *Attorney, Agent, or Firm* — Lerner, David, Littenberg, Krumholz & Mentlik, LLP

(57) ABSTRACT

A spinal implant insertion guide is disclosed. The insertion guide includes at least one channel suitable for receiving and facilitating movement of a spinal implant into an intervertebral space between two vertebrae and a portion suitable for insertion into the intervertebral space. In embodiments for use with spinal implant having multiple pieces, the pieces of the spinal implant remain in cooperation throughout movement. The guide may further include a plunger for facilitating the movement of the spinal implant.

21 Claims, 3 Drawing Sheets

U.S. PATENT DOCUMENTS

| | | |
|---|---|---|
| 6,478,800 B1 | 11/2002 | Fraser et al. |
| 6,520,967 B1 | 2/2003 | Cauthen |
| 6,565,574 B2 | 5/2003 | Michelson |
| 6,575,981 B1 | 6/2003 | Boyd et al. |
| 6,589,247 B2 | 7/2003 | McGahan et al. |
| 6,595,995 B2 | 7/2003 | Zdeblick et al. |
| 6,648,895 B2 | 11/2003 | Burkus et al. |
| 6,652,533 B2 | 11/2003 | O'Neil |
| 6,679,887 B2 | 1/2004 | Nicholson et al. |
| 6,682,534 B2 | 1/2004 | Patel et al. |
| 6,723,096 B1 | 4/2004 | Dorchak et al. |
| 6,730,124 B2 | 5/2004 | Steiner |
| 6,743,234 B2 | 6/2004 | Burkus et al. |
| 6,755,839 B2 | 6/2004 | Van Hoeck et al. |
| 6,770,074 B2 | 8/2004 | Michelson |
| 6,800,093 B2 | 10/2004 | Nicholson et al. |
| 6,814,737 B2 | 11/2004 | Cauthen |
| 6,824,565 B2 | 11/2004 | Muhanna et al. |
| 6,835,208 B2 | 12/2004 | Marchosky |
| 6,855,148 B2 | 2/2005 | Foley et al. |
| 6,875,213 B2 | 4/2005 | Michelson |
| 6,896,680 B2 | 5/2005 | Michelson |
| 6,966,912 B2 | 11/2005 | Michelson |
| 7,326,250 B2 * | 2/2008 | Beaurain et al. ............ 623/17.14 |
| 7,575,576 B2 * | 8/2009 | Zubok et al. .................... 606/90 |
| 2002/0013588 A1 | 1/2002 | Landry et al. |
| 2002/0032483 A1 | 3/2002 | Nicholson et al. |
| 2002/0045944 A1 | 4/2002 | Muhanna et al. |
| 2002/0055745 A1 | 5/2002 | McKinley et al. |
| 2002/0116009 A1 | 8/2002 | Fraser et al. |
| 2002/0123753 A1 | 9/2002 | Michelson |
| 2002/0138145 A1 | 9/2002 | Marchosky |
| 2002/0143343 A1 | 10/2002 | Castro |
| 2002/0161366 A1 | 10/2002 | Robie et al. |
| 2002/0193802 A1 | 12/2002 | Zdeblick et al. |
| 2002/0198532 A1 | 12/2002 | Michelson |
| 2003/0028197 A1 | 2/2003 | Hanson et al. |
| 2003/0097181 A1 | 5/2003 | Castro et al. |
| 2003/0130662 A1 | 7/2003 | Michelson |
| 2003/0144736 A1 | 7/2003 | Sennett |
| 2003/0149438 A1 | 8/2003 | Nichols et al. |
| 2003/0195629 A1 | 10/2003 | Pafford et al. |
| 2003/0233147 A1 | 12/2003 | Nicholson et al. |
| 2003/0236526 A1 * | 12/2003 | Van Hoeck et al. ............. 606/90 |
| 2004/0002758 A1 | 1/2004 | Landry et al. |
| 2004/0030387 A1 | 2/2004 | Landry et al. |
| 2004/0097932 A1 | 5/2004 | Ray et al. |
| 2004/0133278 A1 | 7/2004 | Marino et al. |
| 2004/0143332 A1 | 7/2004 | Krueger et al. |
| 2004/0153089 A1 | 8/2004 | Zdeblick et al. |
| 2004/0225295 A1 | 11/2004 | Zubok et al. |
| 2004/0243240 A1 | 12/2004 | Beaurain et al. |
| 2005/0043740 A1 | 2/2005 | Haid et al. |
| 2005/0043741 A1 | 2/2005 | Michelson |
| 2005/0075643 A1 | 4/2005 | Schwab et al. |
| 2005/0075644 A1 | 4/2005 | DiPoto et al. |
| 2005/0107881 A1 | 5/2005 | Alleyne et al. |
| 2005/0131416 A1 | 6/2005 | Jansen et al. |
| 2005/0131541 A1 | 6/2005 | Trieu |
| 2005/0143747 A1 | 6/2005 | Zubok et al. |
| 2005/0154463 A1 | 7/2005 | Trieu |
| 2005/0165408 A1 | 7/2005 | Puno et al. |
| 2005/0165486 A1 | 7/2005 | Trieu |
| 2005/0192671 A1 | 9/2005 | Bao et al. |
| 2006/0004377 A1 | 1/2006 | Keller |
| 2007/0156243 A1 * | 7/2007 | Errico et al. ................ 623/17.14 |
| 2008/0046084 A1 * | 2/2008 | Sledge ........................ 623/17.16 |

* cited by examiner

INSERTION GUIDE FOR A SPINAL IMPLANT

CROSS-REFERENCE TO RELATED APPLICATIONS

This application is a divisional of U.S. application Ser. No. 11/204,062, filed on Aug. 15, 2005, now abandoned, which claims the benefit of the filing date of U.S. Provisional Patent Application No. 60/601,461 filed Aug. 13, 2004, the disclosures of which are hereby incorporated herein by reference.

BACKGROUND OF THE INVENTION

The present invention relates generally to apparatus and methods for use in spinal disc arthroplasty, and more particularly, to apparatus and methods for use in the insertion of disc replacement implants into the intervertebral space between two adjacent vertebrae.

Whether due to injury, wear, or genetic defect, intervertebral disc degeneration is a problem suffered by many people. Typically, this spinal problem has been addressed by removing the disc material and replacing it with a spinal implant which fuses two adjacent vertebrae. Recently, however, there has been a significant amount of activity directed toward filling the intervertebral space with spinal implants that permit relatively natural movement of the two adjacent vertebrae with respect to each other. In other words, it is now becoming relatively common to utilize disc replacement implants which act like normal functioning spinal discs.

During a standard spinal disc arthroplasty, the damaged spinal disc material is removed and the two adjacent vertebrae are distracted to a distance sufficient to receive the spinal implant. Regardless of the type or size of implant utilized during spinal disc arthroplasty, one of the most difficult steps involves implanting the spinal implant in the intervertebral space. Often, a surgeon will struggle with properly inserting the spinal implant between two vertebrae. This is because inserting the implant requires moving the implant into the intervertebral space, while simultaneously distracting or spreading the two vertebrae. Heretofore, instruments utilized in this process have been rather cumbersome and difficult to manipulate, especially when implanting the aforementioned disc replacement implants.

For the foregoing reasons, there exists a need for an insertion guide for and a method of inserting a disc replacement implant into an intervertebral space.

SUMMARY OF THE INVENTION

In one preferred embodiment of the present invention, a spinal implant insertion guide includes at least one channel adapted for receiving and facilitating movement of at least two cooperating pieces of a spinal implant and a portion suitable for insertion into the intervertebral space between two vertebrae. The portion suitable for insertion into the intervertebral space is a projecting portion having a sloped height and a rounded end. This shape allows the portion to be easily inserted between the two vertebrae. After the projecting portion has been inserted between two vertebrae, the channel desirably extends into the intervertebral space, thereby allowing the implant to be implanted therein. The two pieces of the spinal implant may remain in cooperation with each other throughout movement in the at least one channel, however, slight movement of the pieces may be possible. There may be several embodiments relating to this aspect of the invention. For example, the channel may further include slots for positioning the pieces of the spinal implant in cooperation with one another. The insertion guide according to this embodiment of the present invention may also include a plunger for facilitating the movement of the spinal implant pieces. The portion suitable for insertion into the intervertebral space between two vertebrae may cause distraction of the two vertebrae upon insertion. In certain embodiments, the insertion guide may be packaged with the spinal implant preloaded therein. In other preferred embodiments, the spinal implant may be loaded into the insertion guide immediately before a surgical procedure. The insertion guide may be constructed of a broad range of biocompatible materials such as stainless steel. In certain preferred embodiments, the insertion guide is made of a polymeric material, thereby making it relatively inexpensive to construct and disposable.

Another preferred embodiment of the present invention includes a spinal implant insertion guide having at least one channel suitable for receiving and facilitating movement of a spinal implant, the at least one channel extending into an intervertebral space between two vertebrae. The insertion guide desirably includes a portion suitable for insertion into the intervertebral space, and a plunger for facilitating the movement of the spinal implant into the intervertebral space. This embodiment of the present invention may be configured to allow for the insertion of a spinal implant of unitary construction.

Yet another preferred embodiment of the present invention is a disposable spinal implant insertion guide including at least one channel suitable for receiving and facilitating movement of a spinal implant, the at least one channel extending into an intervertebral space between two vertebra, and a portion suitable for insertion into the intervertebral space. The disposable insertion guide according to this embodiment may be constructed from a broad range of materials including stainless steel or other metals. In one preferred embodiment, the insertion guide is made of a polymeric material.

Another preferred embodiment of the present invention provides a spinal insertion guide kit. The kit desirably includes at least two insertion guides, the at least two insertion guides being of different dimensions. Each guide includes at least one channel suitable for receiving and facilitating movement of at least two cooperating pieces of a spinal implant, the at least one channel extending into an intervertebral space between two vertebrae. Each guide also includes a portion suitable for insertion into the intervertebral space. The pieces of the spinal implant remain in cooperation throughout movement in the at least one channel. In certain embodiments according to this aspect of the present invention, the at least two insertion guides have different sized projecting portions suitable for insertion into the intervertebral space. In other embodiments according to this aspect of the present invention, the at least two insertion guides have different sized channels.

In another preferred embodiment of the present invention, a method of inserting an at least two piece spinal implant includes providing an insertion guide having at least one channel, inserting at least a portion of the insertion guide into an intervertebral space between two vertebrae, placing the at least two piece spinal implant into the at least one channel such that the spinal implant pieces cooperate with one another, and moving the spinal implant pieces together into the intervertebral space. The implant pieces preferably remain in cooperation throughout their insertion. The method according to this aspect of the present invention may also include distracting the vertebrae and/or preparing the vertebrae for receiving the spinal implant. The method may also include stabilizing the guide with respect to the vertebrae, with or without an external support. Finally, this method may also include providing and utilizing a plunger for facilitating the movement of the implant.

Yet another preferred embodiment of the present invention includes a method of implanting a spinal implant of unitary construction. The method according to this embodiment includes providing an insertion guide having at least one channel, inserting at least a portion of the insertion guide into an intervertebral space between two vertebrae, placing the spinal implant into the at least one channel, and moving the spinal implant into the intervertebral space by manipulating a plunger in the at least one channel.

Yet another embodiment of the present invention includes a method of implanting a multi-piece spinal implant. The method according to this embodiment includes providing an insertion guide having at least one channel, inserting at least a portion of the guide into an intervertebral space between two vertebrae, and moving the pieces through the at least one channel into the intervertebral space. During this movement of the pieces into the intervertebral space, the pieces are capable of slight movement with respect to each other.

A preferred method in accordance with the present invention may be a method of inserting a multi-piece spinal implant. This method may include the steps of providing an insertion guide defined by a channel having at least two slots therein, inserting at least a portion of the insertion guide into an intervertebral space between two vertebrae, placing each piece of the multi-piece spinal implant into the channel such that each implant piece engages at least one slot and the spinal implant pieces cooperate with on another, and moving the spinal implant pieces into the intervertebral space while maintaining the spinal implant pieces in cooperation with one another and allowing slight movement of the spinal implant pieces with respect to each other.

A preferred multi-piece spinal implant insertion guide in accordance with the present invention may include a channel including at least two slots, each of the at least two slots capable of engaging a different portion of a multi-piece spinal implant, and at least one extension suitable for insertion into an intervertebral space. Preferably, the guide should be configured so that the pieces of the multi-piece spinal implant remain in cooperation throughout movement in the channel and are capable of slight movement with respect to each other.

Yet another preferred multi-piece spinal implant insertion guide in accordance with the present invention may include a channel including at least two slots, each of the at least two slots capable of engaging a different portion of a multi-piece spinal implant, at least one extension suitable for insertion into an intervertebral space, and a plunger for facilitating movement of the spinal implant pieces. Preferably, the guide should be configured so that the pieces of the multi-piece spinal implant remain in cooperation throughout movement in the channel and are capable of slight movement with respect to each other.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

In describing the preferred embodiments of the subject matter illustrated and to be described with respect to the drawings, specific terminology will be used for the sake of clarity. However, the invention is not intended to be limited to the specific terminology and includes all technical equivalence which operates in a similar manner to accomplish a similar purpose.

Figure 1:
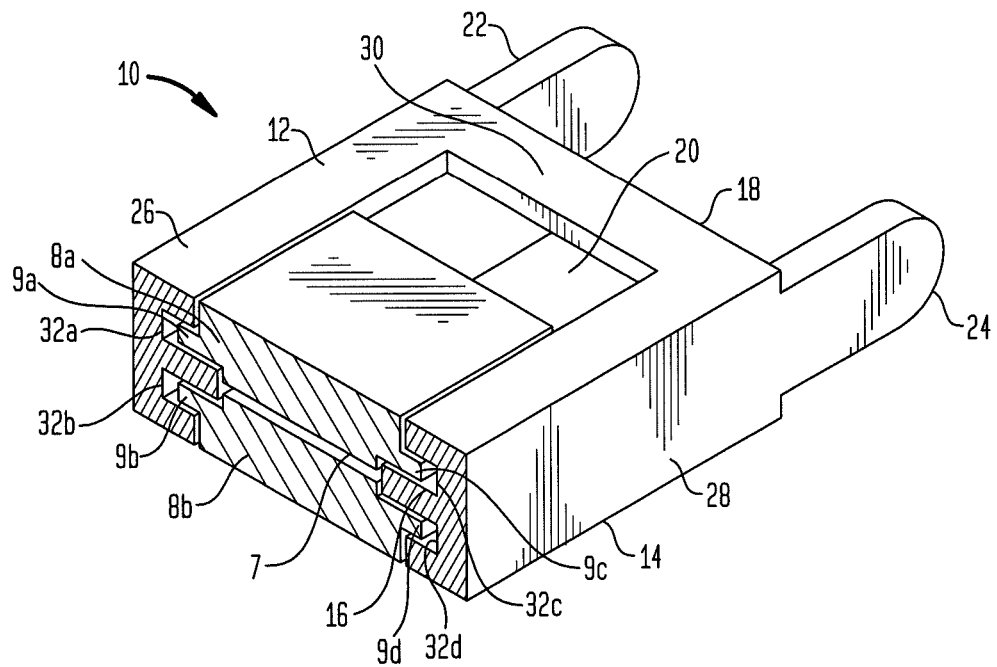
FIG. 1 is a top perspective view of a spinal implant insertion guide according to an embodiment of the present invention.
Figure 2:
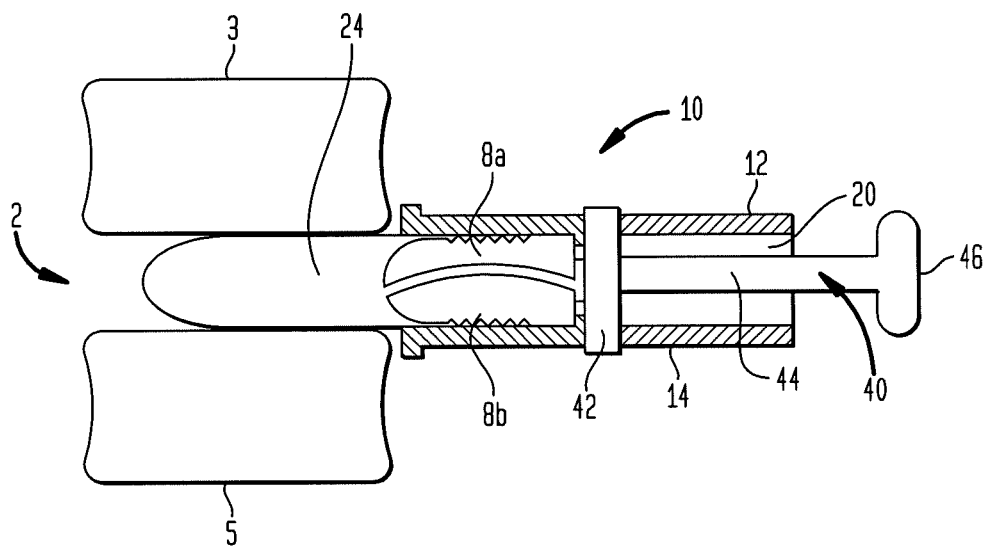
FIG. 2 is a side cross sectional view of the spinal implant insertion guide shown in FIG. 1.
Figure 3:
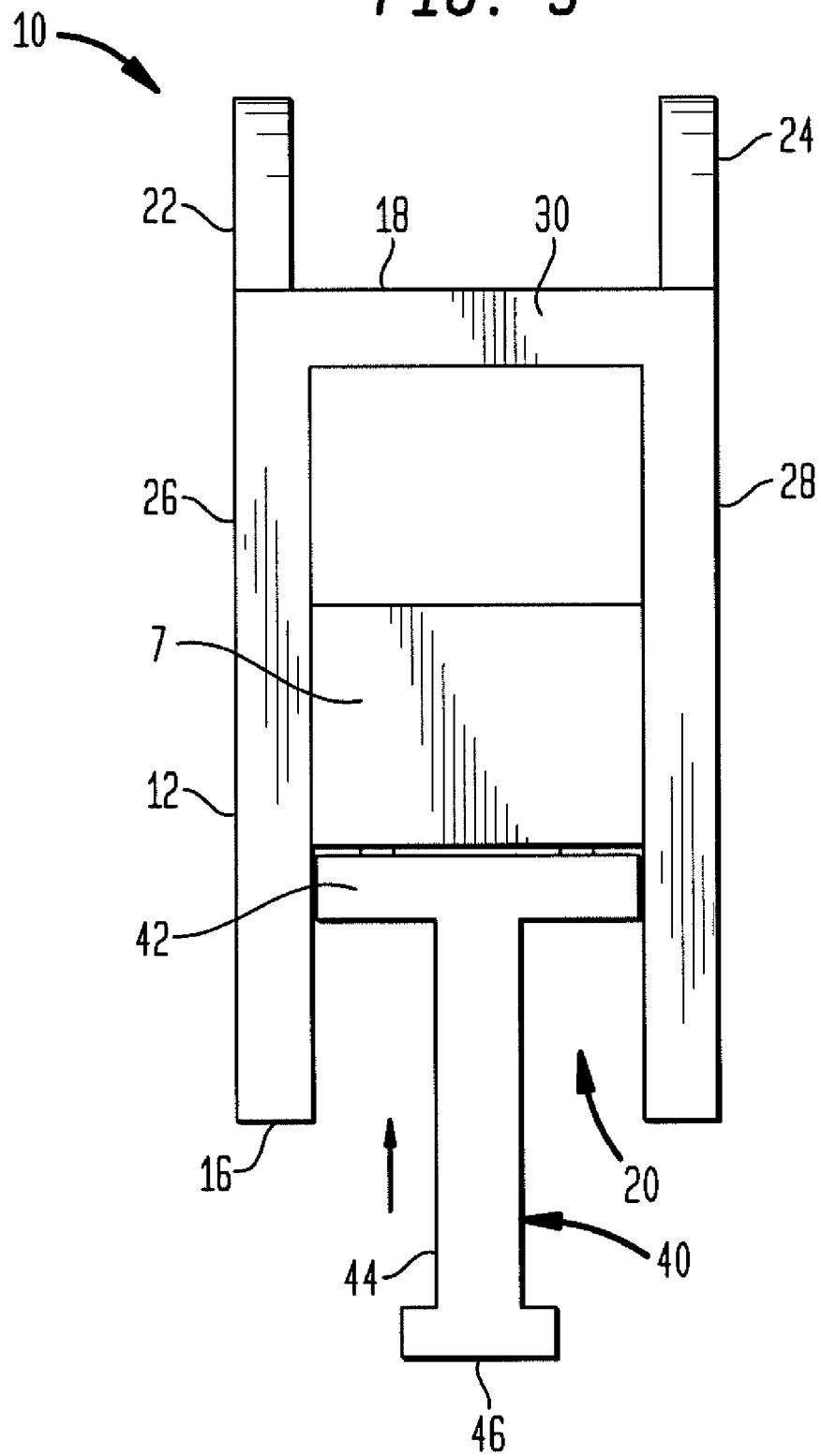
FIG. 3 is a top plan view of the spinal implant insertion guide shown in FIG. 1.

Referring to the drawings, wherein like reference numerals represent like elements, there is shown in FIGS. 1-3, in accordance with an embodiment of the present invention, an insertion guide for a spinal implant designated generally by reference numeral 10. In the preferred embodiment shown in the figures, insertion guide 10 is designed to be used in aiding in the insertion of a spinal implant 7. As best shown in FIG. 1, insertion guide 10 is of unitary construction having a top side 12, a bottom side 14, a proximal end 16, and a distal end 18. Guide 10 also includes a channel 20 adapted to receive a spinal implant 7, and intervertebral extensions 22 and 24 that project from the distal end 18 of insertion guide 10. Guide 10 is adapted for being inserted between two adjacent vertebrae 3 and 5 during a spinal surgical procedure. The intervertebral extensions and 24 are preferably inserted into the intervertebral space 2 for distracting the adjacent vertebrae 3 and 5, as shown in FIG. 2. However, it is noted that extensions 22 and can be sized so that their insertion does not distract vertebrae 3 and 5.

Channel 20 is an opening within guide 10 configured and dimensioned to receive and allow sliding movement of spinal implant 7 from the proximal end 16 toward the distal end 18. As best shown in FIG. 2, the sliding movement allows insertion of implant 7 into intervertebral space 2 between vertebrae 3 and 5. Channel 20 is defined by first lateral wall 26, second lateral wall 28, and distal end wall 30. Distal end wall 30 preferably connects first wall 26 to second wall 28. In the particular preferred embodiment shown in FIG. 1, the guide 10 includes a channel 20 capable of receiving a multi-piece spinal implant 7 having two pieces 8a and 8b. In order to facilitate this reception, channel 20 further includes four slots, 32a and 32b which are cut into first wall 26 and 32c and 32d which are cut into second wall 28. The slots are preferably cut into the inner faces of the first and second lateral walls 26 and 28. Slots 32a and 32c engage and allow for portions 9a and 9c of piece 8a and slots 32b and 32d engage and allow for portions 9b and 9d of piece 8b to ride through channel 20, while remaining in cooperation with one another. In certain embodiments, a second distal end wall may be located directly below posterior wall 30 to provide even more stability between the first and second lateral walls. Preferably, implant 7 is sized so that its height is less than the distance between posterior wall 30 and any second posterior end wall located directly below wall (not shown). Thus, a clearance between the implant and these walls exists, and implant 7 can be moved through channel 20.

Intervertebral extensions 22 and 24 are preferably narrower in height than the height of the first lateral wall 26 and second lateral wall 28, respectively. Extensions 22 and 24 extend beyond the portion of the first and second walls at which distal end wall 30 intersects them. As best shown in FIGS. 1 and 2, extensions 22 and 24 preferably increase in height in a direction from the distal end 18 toward the proximal end 16. In the embodiment shown, the distal ends of extensions 22, 24 are rounded in order to facilitate easy insertion into the space between the two vertebrae, and are spread to cause distraction of vertebrae 3 and 5 upon insertion. However, the distal ends of extensions and 24 may be of any shape. As mentioned above, in certain preferred embodiments, extensions 22, 24 may sized to distract or properly fit between the two vertebrae 3 and 5. A result of the latter construction is that the two vertebrae are not distracted upon insertion of the extensions 22, 24 therebetween. This may be useful in a surgery in which a separate distraction tool is utilized.

Preferably, as shown in FIG. 3, extensions 22, 24 each have a width which creates a space between the two extensions large enough to allow passage of implant 7 therethrough. In other words, in the preferred embodiment, implant pieces 8a and 8b are preferably allowed to ride along slots 32a, 32b, 32c and 32d and past extensions 22, 24 during insertion between vertebrae 3 and 5. Preferably, once implant pieces 8a and 8b pass through the slots, the forced cooperation of the pieces is retained by way of vertebrae 3 and 5. Thus, extensions 22, 24 are not required to contact any portion of implant 7. However, it is contemplated to provide slots, like slots 32a, 32b, 32c and 32d, which continue along the length of extensions 22, 24. Therefore, these slots would guide and retain implant pieces 8a and 8b in cooperation with one another throughout the entire passage through guide 10.

As best shown in FIGS. 2 and 3, guide 10 may be fitted with a plunger or driver 40. Plunger 40 includes a channel sized end 42, an elongate shaft 44, and a handle 46. Channel sized end 42, as shown in FIGS. 2 and 3, is sized to fit snuggly within channel 20, while also being capable of contacting implant 7. Handle 46 is an easily operable handle, which allows a surgeon to facilitate movement of plunger 40. Handle 46 preferably has a wide variety of designs, including ergonomic designs and thumb operable designs. Elongate shaft 44 creates a connection between end and handle 46. In certain preferred embodiments the elongate shaft 44 is dimensioned in length to allow for the full implantation of implant 7 within intervertebral space 2, without the introduction of handle 46 into channel 20.

Another aspect of the present invention is a method for inserting a spinal implant into an intervertebral space. The method according to this aspect of the invention includes the step of providing an insertion guide as discussed above. It is noted that the guide can be in accordance with any of the various embodiments disclosed herein, as the particular design may not cause the standard method step to significantly deviate. For the sake of ease in explaining the method, insertion guide 10 will be utilized below.

Initially, intervertebral extensions 22 and 24 of guide 10 are inserted between vertebrae 3 and 5. Depending upon the dimensions of extensions 22 and 24, the insertion of such may cause distraction of vertebrae 3 and 5 from one another. A surgeon may simply utilize his own bare hands to push extensions 22 and 24 into intervertebral space 2, or other tools such as hammers and mallets may be utilized, as for example in situations where vertebrae 3 and 5 are distracted during insertion of the guide. This distraction is accomplished by utilizing the rounded ends and/or sloped nature of the extensions to slowly insert guide 10 between vertebrae 3 and 5 to simultaneously distract the same. However, as mentioned above, extensions 22 and 24 need not be sized for such distraction and can be dimensioned to allow for a snug fit between vertebrae 3 and 5 without causing significant distraction.

In certain embodiments, vertebrae 3 and 5 may be prepared to receive an implant prior to the insertion of extensions 22 and 24. Depending upon the type of implant, this may include the removal of the deteriorated or damaged disc material, and/or the shaping of the bone to better receive the implant. For example, when utilizing implants that include keels, spikes or other protrusions, it may be necessary to cut channels or otherwise remove bone from vertebrae 3 and 5 to allow for proper implantation of the implant. It is also contemplated that once guide 10 is inserted between vertebrae 3 and 5, it may be supported by means other than the snug connection between the vertebrae. For example, an external support may be utilized to support guide 10 outside of the vertebrae. However, it is noted that often times, the fit of extensions 22, 24 between vertebrae 3 and 5 and the pressure exerted thereby is enough hold guide 10 in place.

Subsequent to guide 10 being inserted into intervertebral space 2, spinal implant 7 is preferably then placed into channel 20. It is also possible to pre-seat spinal implant 7 within channel 20, prior to guide 10 being inserted between the vertebrae. The latter design may be important in providing prepackaged, easily autoclaved or otherwise sterilized individual units. Regardless of when implant 7 is placed into channel 20, the inserted position of guide 10 allows for the implant to be moved into intervertebral space 2. For embodiments in which a spinal implant having two or more pieces is being implanted, it should be noted that the multiple pieces are placed into the insertion guide so that they cooperate with one another (e.g.—their articulating surfaces mate), and remain in this cooperation throughout their movement into the intervertebral space. It should also be noted that while pieces 8a and 8b of implant 7 are in cooperation with each other, these pieces may be capable of slightly moving with respect to each other. This slight motion may aid in the insertion of implant 7. For example, the slight motion may allow a surgeon to better manipulate pieces 8a and 8b to overcome hindrances caused by the adjacent vertebrae.

In a preferred embodiment, guide 10 is configured and dimensioned so as to allow for the above noted slight movement of pieces 8a and 8b of implant 7 with respect to each other. More particularly, channel 20 and slots 32a, 32b, 32c and 32d may be configured and dimensioned to allow for enough clearance so that slight canting of implant pieces 8a and 8b, or slight translation of the two implant pieces may be accomplished. In certain embodiments, the slots may simply be larger than the portions of pieces 8a and 8b being inserted therein. This would create a clearance that may allow for the two implant pieces to be moved with respect to one another. It is noted that any movement of pieces 8a and 8b with respect to each other should be such that the articulation surfaces of the two pieces remain in cooperation with each other. For example, the movement may be slight movement that is merely a portion of that which is allowed by the aforementioned articulation surfaces of pieces 8a and 8b. As mentioned above, allowing such slight movement may aid a surgeon during the implantation of implant 7. However, in certain cases, such movement may not be necessary.

The movement of spinal implant 7 into intervertebral space 2 is accomplished by applying a force to push the implant through channel 20 of the guide 10 and into the space. This force may be provided by utilizing a plunger 40, as described above. In these embodiments, plunger 40 is inserted into channel 20 subsequent to the placing of implant therein. Once again, in the prepackaged units mentioned above, plunger 40 may be packaged in an inserted position. Operation of handle 46 allows a surgeon to more easily push implant 7 into intervertebral space 2. In certain preferred embodiments, the sizing of plunger 40 should be such that the channel sized end 42 can fully situate implant 7 into intervertebral space 2, without handle 46 entering channel 20. Once implant 7 is moved into intervertebral space 2, guide 10 may be removed from its position between vertebrae 3 and 5. Thereafter, implant 7 may be seated in intervertebral space 2 in accordance with standard practices relating to the particular implant. For example, the individual pieces 8*a* and 8*b* of spinal implant 7 may both be cemented to adjacent vertebrae. However, it is also contemplated that various implants may have many different manners of being seated within an intervertebral space. For example, certain spinal implants may include flanges for facilitating connection with a bone screw or keels/spikes for implantation into the vertebral endplates. It is noted that in certain embodiments, end 42 of plunger 40 may be operatively connected to implant 7, or in other embodiments, may merely be capable of abutting the implant.

In certain embodiments, extensions 22 and 24 are sized so that insertion between vertebrae 3 and 5 causes distraction. However, this is not necessary. In embodiments in which the extensions are sized to facilitate distraction, the sloped configuration of extensions 22 and 24 allows for the increase of distraction of the vertebrae with respect to the further insertion of the extensions between the vertebrae. Upon implantation of implant 7, guide 10 may be removed. Similarly, guide 10 may be removed prior to the fixation of implant 7 to vertebrae 3 and 5, respectively. In embodiments in which extensions 22 and 24 are sized and configured to cause distraction of vertebrae 3 and 5, removal of guide 10 may cause the vertebrae to return to their non-distracted position, thereby clamping and/or seating implant 7 in place. For implants that utilize keels or spikes, this vertebrae movement may cause the projections to become seated in their respective vertebrae.

Figure 4:
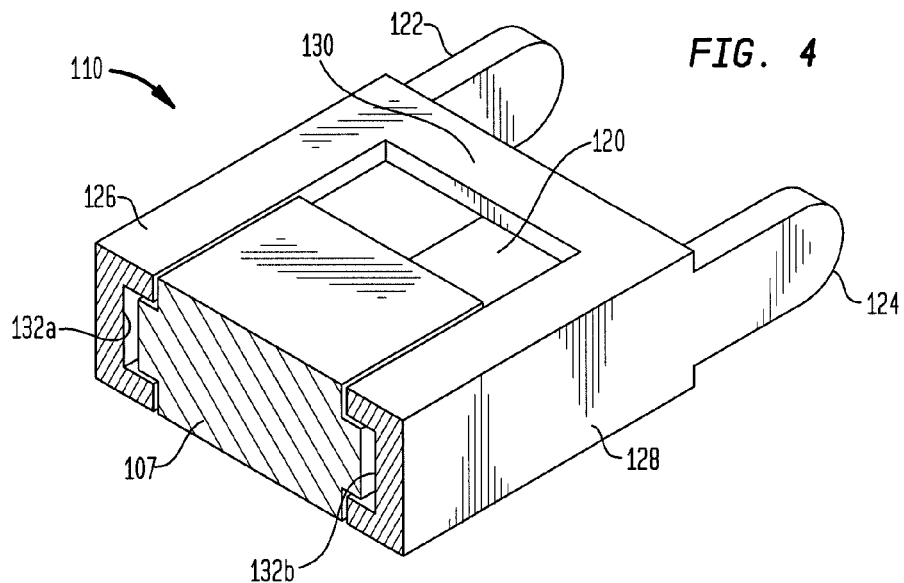
FIG. 4 is a top perspective view of a spinal implant insertion guide according to another embodiment of the present invention.
Figure 5:
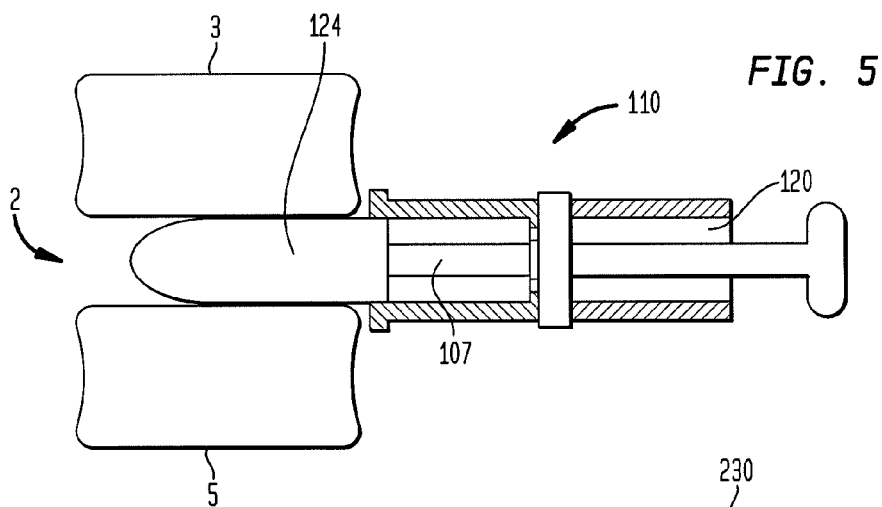
FIG. 5 is a side cross sectional view of the spinal implant insertion guide shown in FIG. 4.

FIGS. 4 and 5 depict an insertion guide 110 used for inserting single piece implant 107 in accordance with other preferred embodiments of the present invention. As shown in these figures, guide 110 is similar in design to guide 10, the only deviation in design residing in the inclusion of only two slots 132*a* and 132*b*, as opposed to the four slots of guide 10. As in the design of guide 10, slots 132*a* and 132*b* are cut into first lateral wall 126 and second lateral wall 128. Also as in guide 10, guide 110 may be utilized in conjunction with a properly sized and dimensioned plunger 40, in a manner like that disclosed above.

Figure 6:
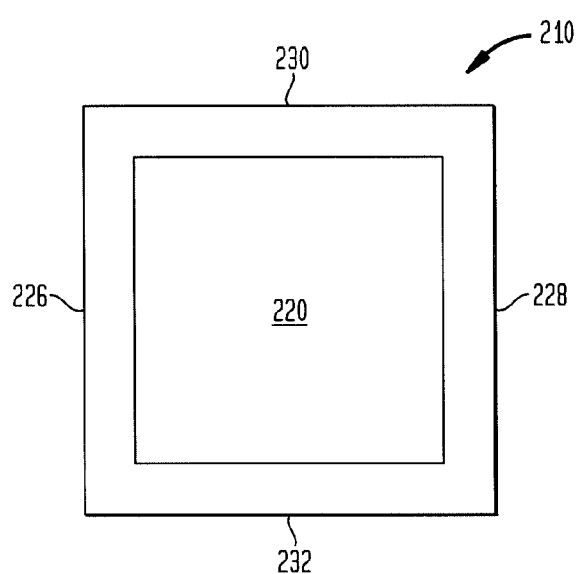
FIG. 6 is a front plan view of a spinal implant insertion guide according to another embodiment of the present invention.

It is also contemplated that while the designs of both guide 10 and guide 110 include at least two slots for receiving and holding the spinal implant, designs are envisioned that do not require slots. For example, as shown in FIG. 6, a guide 210 includes an enclosed channel 220 for receiving a spinal implant. Walls 226, 228, 230, and 232 define channel 220, and rid guide 210 of the need for any slots. Rather than the substantially square cross section of guide 220, other guides may include cross sections that better suit the cross section of particular spinal implants. For example, guides having a rectangular cross section may be employed. Similarly, the exterior surface of certain embodiments of the present invention may be shaped to allow for the easier insertion of the guide through an incision. For example, the exterior surface of a guide may be rounded. Once again, guide 210, like guides 10 and 100, can be used in conjunction with a properly sized and dimensioned plunger 40, in a manner like that disclosed above. Finally, it is noted that any of the above guides and/or each of their respective elements and components may be constructed of any type of material suitable for insertion into the human body. For example, it is contemplated to construct any of the guides and/or plungers of metals such as stainless steel. In addition, these devices may be constructed of polymers.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of inserting a multi-piece spinal implant comprising:
   providing an insertion guide having:
      a channel defined by a first lateral wall extending along a first plane, and a second lateral wall extending along a second plane, each lateral wall having at least two slots thereon; and
      distal end walls extending along third and fourth planes, respectively, wherein the third and fourth planes are parallel to one another and perpendicular to the first and second planes;
   inserting at least a portion of the insertion guide into an intervertebral space between two vertebrae;
   placing each piece of the multi-piece spinal implant into the channel such that each implant piece engages at least one slot and the spinal implant pieces cooperate with one another;
   moving the spinal implant pieces through the channel and into the intervertebral space while maintaining the spinal implant pieces in cooperation with one another and allowing slight canting of the spinal implant pieces with respect to each other while in the channel;
   wherein said insertion guide further includes at least one extension for insertion into the intervertebral space; and
   wherein the at least one extension projects from the first lateral wall, and wherein the slots in the first lateral wall extend along the entire length of the first lateral wall and the extension.

2. The method according to claim 1, wherein said inserting step includes distracting the vertebrae.

3. The method according to claim 1, further including the step of preparing each vertebrae for receiving the spinal implant.

4. The method according to claim 1, further including the step of stabilizing the insertion guide with respect to the vertebrae.

5. The method according to claim 4, wherein the stabilization is achieved by supporting the insertion guide outside of the vertebrae.

6. The method according to claim 4, wherein the stabilization is achieved by supporting the insertion guide within the vertebrae.

7. The method according to claim 1, wherein the insertion guide further includes a plunger.

8. The method according to claim 7, wherein said moving step includes manipulating the plunger to move the spinal implant pieces.

9. The method according to claim 8, wherein the plunger is inserted into the channel subsequent to the spinal implant pieces.

10. The method according to claim 1, wherein said placing step is performed prior to said inserting step.

11. The method according to claim 1, wherein the slots in the first and second lateral walls are configured to permit slight canting of the implant pieces with respect to one another, while the multi-piece implant is moved through the channel.

12. A method of inserting a multi-piece implant comprising:
providing an insertion guide having:
a channel defined by a first lateral wall extending along a first plane, and a second lateral wall extending along a second plane, each lateral wall having at least two slots thereon; and
distal end walls extending along third and fourth planes, respectively, wherein the third and fourth planes are parallel to one another and perpendicular to the first and second planes;
inserting at least a portion of the insertion guide into an intervertebral space between two vertebrae;
placing each piece of the multi-piece implant into the channel such that each implant piece engages at least one slot and the implant pieces cooperate with one another;
providing a plunger having a handle, a shaft extending from the handle and a distal end for contacting the implant;
contacting the distal end of the plunger with an opposing face of the implant;
applying a force to the distal end of the plunger while maintaining the implant pieces in cooperation with one another and allowing slight canting of the implant pieces with respect to each other, while in the channel, to move the multi-piece implant into the intervertebral space;
wherein said insertion guide further includes at least one extension for insertion into the intervertebral space; and
wherein the at least one extension projects from the first lateral wall, and wherein the slots in the first lateral wall extend along the entire length of the first lateral wall and the extension.

13. The method according to claim 12, wherein said inserting step includes distracting the vertebrae.

14. The method according to claim 12, wherein said contacting step includes interconnecting the distal end of the plunger with the opposing face of the implant.

15. The method according to claim 12, further including the step of stabilizing the insertion guide with respect to the vertebrae.

16. The method according to claim 15, wherein the stabilization is achieved by supporting the insertion guide outside of the vertebrae.

17. The method according to claim 15, wherein the stabilization is achieved by supporting the insertion guide within the vertebrae.

18. The method according to claim 12, wherein the plunger is inserted into the channel subsequent to the spinal implant pieces.

19. The method according to claim 12, wherein said placing step is performed prior to said inserting step.

20. The method according to claim 12, wherein a second extension projects from the second lateral wall, and wherein the slots in the second lateral wall extend along the entire length of the second lateral wall and the second extension.

21. The method according to claim 12, wherein the slots in the first and second lateral walls are configured to permit slight canting of the implant pieces with respect to one another, while the multi-piece implant is moved through the channel.

* * * * *